(12) United States Patent
Hupperts et al.

(10) Patent No.: US 6,218,565 B1
(45) Date of Patent: Apr. 17, 2001

(54) METHOD FOR PRODUCING N-(3-AMINO-4-FLUORO-PHENYL)-SULPHONAMIDES, N-(3-AMINO-4-FLUORO-PHENYL)-CARBOXYLIC ACID AMIDES AND N-(3-AMINO-4-FLUOROPHENYL) CARBAMATES

(75) Inventors: Achim Hupperts, Düsseldorf; Reinhard Lantzsch, Wuppertal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/582,911
(22) PCT Filed: Dec. 24, 1998
(86) PCT No.: PCT/EP98/08443
§ 371 Date: Jul. 6, 2000
§ 102(e) Date: Jul. 6, 2000
(87) PCT Pub. No.: WO99/35122
PCT Pub. Date: Jul. 15, 1999

(30) Foreign Application Priority Data

Jan. 9, 1998 (DE) .............................. 198 00 531

(51) Int. Cl.[7] ................ C07C 231/02; C07C 269/04; C07C 303/38
(52) U.S. Cl. ............... 560/13; 560/30; 564/99; 564/176; 564/218
(58) Field of Search ............... 560/13, 30; 564/99, 564/176, 218

(56) References Cited

FOREIGN PATENT DOCUMENTS 0 127 079    12/1984   (EP) .

OTHER PUBLICATIONS

March et al., Advanced Organic Chemistry, etc., McGraw–Hill, pp. 385 and 386, 1968.*
Bull Soc. Chim. Fr. 132, (month unavailable) 1995, pp. 306–313, René Beugelmans et al Sythése d'hétérocycles á 5 et 6 chaînons par une stratégie combinant des réactions $S_NAr$ et $S_{RN}1$.

Recueil Trav. Chim. Pays–Bas 65 (month unavailable) 1946, pp. 329–332, Blanksma et al On the Sweet Taste of the 1–Halogeno–2–Amino–2–Nitrobenzenes.

* cited by examiner

Primary Examiner—Peter O'Sullivan
(74) Attorney, Agent, or Firm—Joseph C. Gil

(57) ABSTRACT

The invention relates to a process for preparing N-(3-amino-4-fluoro-phenyl)-sulphonamides, N-(3-amino-4-fluoro-phenyl)-carboxamides or N-(3-amino-4-fluoro-phenyl)-carbamates of the general formula (I)

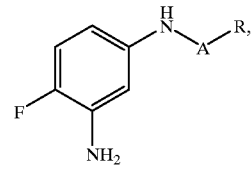

(I)

in which
  A represents $SO_2$, CO or $CO_2$ and
  R represents in each case optionally substituted alkyl or aryl, wherein
  1-fluoro-2,4-diamino-benzene of the formula (II)

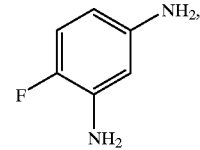

(II)

is reacted with sulphonyl chlorides, carbonyl chlorides or chlororformic esters of the general formula (III)

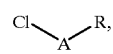

(III)

in which
  A and R are as defined above
in the presence of an acid acceptor and in the presence of a diluent at temperatures between –20° C. and +100° C.

6 Claims, No Drawings

METHOD FOR PRODUCING N-(3-AMINO-4-FLUORO-PHENYL)-SULPHONAMIDES, N-(3-AMINO-4-FLUORO-PHENYL)-CARBOXYLIC ACID AMIDES AND N-(3-AMINO-4-FLUOROPHENYL) CARBAMATES

TECHNICAL FIELD OF THE INVENTION

The invention relates to a novel process for preparing N-(3-amino-4-fluoro-phenyl)-sulphonamides, N-(3-amino-4-fluoro-phenyl)-carboxamides and N-(3-amino-4-fluoro-phenyl)-carbamates which can be used as intermediates for preparing herbicidally active compounds.

BACKGROUND OF THE INVENTION

It is known that N-(3-amino-4-fluoro-phenyl)-sulphonamides are obtained when corresponding N-(3-nitro-4-fluoro-phenyl)-sulphonamides are reacted with reducing or hydrogenating agents, such as, for example, iron in the presence of an acid, such as, for example, acetic acid, or hydrogen in the presence of a catalyst, such as, for example, platinum oxide (cf. EP-A-496595). However, the preparation of the required starting materials by selective reduction of 1-fluoro-2,4-dinitro-benzene and subsequent reaction with sulphonyl chlorides involves technical problems. In particular attempts to hydrogenate 1-fluoro-2,4-dinitro-benzene selectively to 1-fluoro-4-amino-2-nitro-benzene always yield mixtures of the possible monohydrogenated products and the dihydrogenated product. For this reason, 1-fluoro-4-amino-2-nitro-benzene (cf. EP-A-127079; Recueil Trav. Chim. Pays-Bas 65 (1946), 329) (and also 1-fluoro-2,4-diamino-benzene (cf. Bull. Soc. Chim. Fr 132 (1995), 306–313)) are generally prepared by reduction with metals or with metal compounds, such as, for example, with iron in the presence of iron(II) sulphate or in the presence of acetic acid, or with tin(II) chloride in the presence of hydrochloric acid. However, the use of such reducing agents in industry should be avoided, if possible, owing to the associated disposal problems.

Furthermore, it is known that N-(3-amino-4-chloro-phenyl)-sulphonamides and N-(3-amino-4-chloro-phenyl)-carboxamides are obtained when 1-chloro-2,4-diamino-benzene is reacted with sulphonyl chlorides and carbonyl chlorides, respectively (cf. WO-A-9727171). However, the yields and quality of the products in these reactions are not always entirely satisfactory. Since chlorine and fluorine as substituents on arenes frequently have a very different directing effect for further reactions, an analogous reaction of 1-fluoro-2,4-diamino-benzene with sulphonyl chlorides or carbonyl chlorides could furthermore not be expected to be a matter of course.

DETAILED DESCRIPTION OF THE INVENTION

It has now been found that N-(3-amino-4-fluoro-phenyl)-sulphonamides, N-(3-amino-4-fluoro-phenyl)-carboxamides and N-(3-amino-4-fluoro-phenyl)-carbamates of the general formula (I)

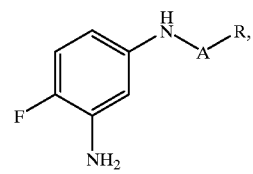

in which
A represents $SO_2$, CO or $CO_2$ and
R represents in each case optionally substituted alkyl or aryl
are obtained in very good yields and in high purity when 1-fluoro-2,4-diamino-benzene of the formula (II)

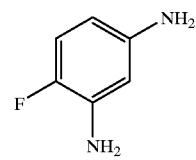

or an acid adduct thereof
is reacted with sulphonyl chlorides, carbonyl chlorides or chloroformic esters of the general formula (III)

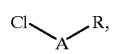

in which
A and R are as defined above
in the presence of an acid acceptor and in the presence of a diluent at temperatures between $-20°$ C. and $+100°$ C.

Surprisingly, it is possible to obtain N-(3-amino-4-fluoro-phenyl)-sulphonamides, N-(3-amino-4-fluoro-phenyl)-carboxamides and N-(3-amino-4-fluoro-phenyl)-carbamates of the general formula (I) in very good yields and in high purity by the process according to the invention, although the formation of approximately equimolar mixtures of the possible "simple" sulphonylation products or acylation products—possibly also contaminated to a relatively large extent by products of multiple sulphonylation or acylation—was to be expected.

It is an advantage of the process according to the invention that the starting material-1-fluoro-2,4-diamino-benzene—can be obtained very easily in one step by catalytic hydrogenation from 1-fluoro-2,4-dinitro-benzene, so that, in contrast to the prior art (cf. EP-A-496595), a further reduction step is no longer required.

A further advantage of the process according to the invention is that the reaction does not have to be carried out in a mixture of different solvents (cf. WO-A-9727171), but that one solvent is sufficient.

Furthermore, it is particularly advantageous that the reaction products of the general formula (I) can in many cases be employed without isolation, i.e. in the reaction mixture of the reaction according to the invention, directly for further conversions, such as, for example, acylations or sulphonylations (with carbonyl chlorides, chloroformic esters, sulphonyl chlorides, etc.), which give pure products in good yields.

The process according to the invention is therefore a useful advance on the prior art.

Using, for example, 1-fluoro-2,4-diamino-benzene and methanesulphonyl chloride as starting materials, the course of the reaction in the process according to the invention can be illustrated by the following formula scheme:

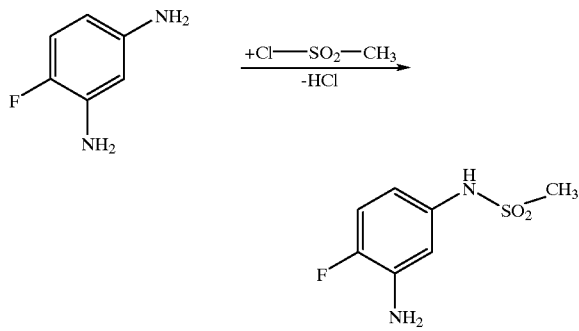

The compound 1-fluoro-2,4-diamino-benzene of the formula (II) to be used as starting material in the process according to the invention is already known (cf. Bull. Soc. Chim. Fr. 132 (1995), 306–313).

The compound of the formula (II) can advantageously be prepared by catalytic hydrogenation of 1-fluoro-2,4-dinitro-benzene.

Suitable for use as acid adducts of the compound of the formula (II) are in particular salts with strong acids, such as hydrochloric acid or sulphuric acid. The mono- and bis-hydrochlorides may be mentioned as being preferred. The formula (III) provides a general definition of the sulphonyl chlorides, carbonyl chlorides and chloroformic esters further to be used as starting materials in the [lacuna] according to the invention. In the formula (III)

A preferably represents $SO_2$, CO or $CO_2$ and

R preferably represents optionally cyano-, halogen- or $C_1$–$C_4$-alkoxy-substituted alkyl having 1 to 6 carbon atoms or preferably represents optionally cyano-, nitro-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkoxy-carbonyl- or di-($C_1$–$C_4$-alkyl)-amino-substituted aryl having 6 or 10 carbon atoms.

In the formula (III)

A in particular represents $SO_2$ or CO and

R in particular represents in each case optionally cyano-, fluorine-, chlorine-, methoxy- or ethoxy-substituted methyl, ethyl, n- or i-propyl, n-, i-, s- or t-butyl, or in particular represents optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, methoxycarbonyl-, ethoxycarbonyl-, n- or i-propoxy-carbonyl-, dimethylamino- or diethylamino-substituted phenyl.

The starting materials of the general formula (III) are known organic chemicals for synthesis.

The process according to the invention is carried out using an acid acceptor. Suitable acid acceptors are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

In the process according to the invention, very particularly preferred acid acceptors are basic organic nitrogen compounds, in particular pyridine.

The process according to the invention is carried out using a diluent. Suitable diluents for carrying out the process according to the invention are—if appropriate in addition to water—especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile propionitrile or butyronitrile; amides, such as N,N-dimethylformamide, N,N-dimethylacetamide, N-methyl-formanilide, N-methyl-pyrrolidone or hexamethyl-phosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, if appropriate also (mono- or polyphasic) mixtures of the above mentioned solvents with water.

In the process according to the invention, very particularly preferred diluents are aprotic polar organic solvents, such as, in particular, acetone, butanone or methyl isobutyl ketone; acetonitrile, propionitrile or butyronitrile.

When carrying out the process according to the invention, the reaction temperatures can be varied within a relatively wide range. In general, the process is carried out at temperatures between –20° C. and +100° C., preferably between –5° C. and +60° C., in particular between +10° C. and +30° C.

The process according to the invention is generally carried out under atmospheric pressure. However, it is also possible to carry out the process according to the invention under elevated or reduced pressure—in general between 0.1 bar and 100 bar.

To carry out the process according to the invention, generally from 0.9 to 1.5 mol, preferably from 1.0 to 1.1 mol, of sulphonyl chloride or carbonyl chloride of the formula (III) and, if appropriate, from 1.0 to 2.0 molar equivalents, preferably from 1.1 to 1.5 molar equivalents, of acid acceptor are employed per mole of 1-fluoro-2,4-diamino- benzene of the formula (II).

In a preferred embodiment of the process according to the invention, the 1-fluoro-2,4-diamino-benzene of the formula (II) is admixed at room temperature (about 20° C.) with a diluent and an acid acceptor, and the sulphonyl chloride, the carbonyl chloride or the chloroformic ester is then metered in with stirring. Alternatively, it is also possible to meter in acid acceptor and sulphonyl chloride, carboxylic chloride or chloroformic ester at the same time ("synchronously", "in parallel"). The reaction mixture is then stirred in the temperature interval indicated until the reaction has ended and can then be worked up by customary methods (cf. the Preparation Examples).

However, it is also possible to react the products of the general formula (I) present in the reaction mixture without intermediate isolation further with sulphonyl chlorides, carbonyl chlorides or chloroformic esters to give compounds of the general formula (IV) (cf. the Preparation Examples)

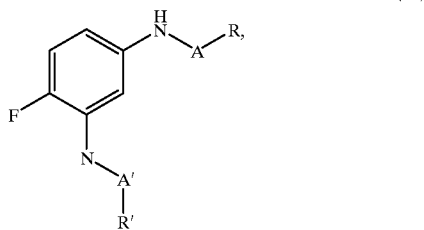

(IV)

in which

A and R are as defined above and

A' and R' have the meanings given above for A and R, respectively, but where the meanings of A and A' and of R and R' do not have to be identical in each individual case.

The compounds of the general formula (I) preparable by the process according to the invention can be used as intermediates for preparing herbicidally active compounds (cf. EP-A-496595).

PREPARATION EXAMPLES

Example 1

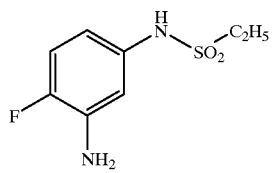

In a 250 ml two-necked flask fitted with internal thermometer, dropping funnel and magnetic stirrer, 6.30 g (0.05 mol) of 1-fluoro-2,4-diamino-benzene are initially charged in 80 ml of acetonitrile and 4.8 g (0.06 mol) of pyridine and, at from 10° C. to 15° C., admixed with 6.43 g (0.05 mol) of ethanesulphonyl chloride. The reaction mixture is stirred at room temperature (about 20° C.) for one hour and admixed with 100 ml of ethyl acetate and 50 ml of water. The organic phase is separated off, the aqueous solution is extracted three times with in each case 50 ml of ethyl acetate and the organic phases are combined, washed with 100 ml of water, dried over sodium sulphate and filtered. The solvent is carefully distilled off from the filtrate under water pump vacuum.

This gives 10.7 g of crude product which, according to GC/MS, contains 92.8% of N-(3-amino-4-fluoro-phenyl)-ethanesulphonamide (i.e. 91% of theory)

Example 2

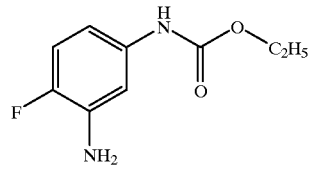

In a 100 ml two-necked flask fitted with internal thermometer, dropping funnel and magnetic stirrer, 3.15 g (25 mMol) of 1-fluro-2,4-diamino-benzene are initially charged in 50 ml of acetonitrile and 2.4 g (30 mMol) of pyridine and, at from 10° C. to 15° C., admixed with 2.7 g (25 mMol) of ethyl chloroformate. The reaction mixture is stirred at room temperature (about 20° C.) for one hour and then admixed with 50 ml of methylene chloride, 50 ml of water and 10 ml of 2N hydrochloric acid. The organic phase is separated off and the aqueous solution is neutralized and extracted three times with in each case 20 ml of methylene chloride. The combined organic phases are washed with 100 ml of water, dried over sodium sulphate and filtered. The solvent is carefully distilled off from the filtrate under water pump vacuum.

This gives 5.4 g of crude product which, according to HPLC, contains 91.8% of O-ethyl N-(3-amino-4-fluoro-phenyl)-carbamate (100% of theory).

Example 3

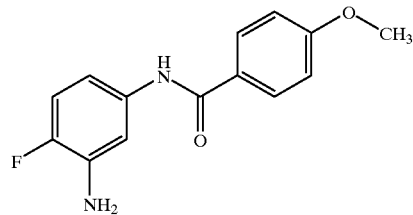

In a 100 ml two-necked flask fitted with internal thermometer, dropping funnel and magnetic stirrer, 3.15 g (25 mMol) of 1-fluoro-2,4-diamino-benzene are initially charged in 50 ml of acetonitrile and 2.4 g (30 mMol) of pyridine and, at from 10° C. to 15° C., admixed with 4.26 g (25 mMol) of 4-methoxy-benzoyl chloride. The reaction mixture is stirred at room temperature (about 20° C.) for one hour and then admixed with 50 ml of ethyl acetate and 50 ml of water. The organic phase is separated off, the aqueous phase is reextracted three times with in each case 20 ml of ethyl acetate and the combined organic phases are washed with 100 ml of water, dried over sodium sulphate and filtered. The solvent is carefully distilled off from the filtrate under water pump vacuum.

This gives 6.1 g of a grey crystalline crude product which, according to HPLC, contains 89.2% of N-(3-amino4-fluoro-phenyl)-4-methoxy-benzamide (84% of theory).

Example 4

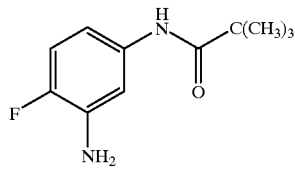

In a 100 ml two-necked flask fitted with internal thermometer, dropping funnel and magnetic stirrer, 3.15 g (25 mMol) of 1-fluoro-2,4-diamino-benzene are initially charged in 80 ml of acetonitrile and 2.4 g (30 mMol) of pyridine and, at 5° C., admixed with 3.01 g (25 mMol) of pivaloyl chloride. The reaction mixture is stirred at room temperature (about 20° C.) for one hour and admixed with 570 Fill Cf ethyl acetate and 50 ml of water. The organic phase is separated off, the aqueous phase is reextracted three times with in each case 20 ml of ethyl acetate and the combined organic phases are washed with 100 ml of water, dried over sodium sulphate and filtered. The solvent is carefully distilled off from the filtrate under water pump vacuum.

This gives 5.2 g of a brown solid which, according to HPLC, contains 82.7% of N-(3-amino-4-fluoro-phenyl)-pivalamide (82% of theory).

Example 5

In a 250 ml two-necked flask fitted with internal thermometer, dropping funnel and magnetic stirrer, 6.30 g (50 mMol) of 1-fluoro-2,4-diamino-benzene are initially charged in 80 ml of acetonitrile and 11.8 g (150 mMol) of pyridine and, at from 10° C. to 15° C., admixed with 6.43 g (50 mMol) of ethanesulphonyl chloride. The reaction mixture is stirred at room temperature (about 20° C.) for one hour and then admixed with 5.97 g (55 mMol) of ethyl chloroformate. Stirring is continued at room temperature for one hour, and the reaction mixture is admixed with 100 ml of ethyl acetate and 50 ml of water and the phases are separated. The aqueous phase is extracted three times with in each case 50 ml of ethyl acetate and the combined organic phases are washed with 100 ml of water, dried over sodium sulphate and filtered. The solvent is carefully distilled off from the filtrate under water pump vacuum.

This gives 15.6 g of a crystalline crude product which, according to HPLC, contains 89.1% of N-(3-ethoxycarbonylamino-4-fluoro-phenyl)-ethanesulphonamide (96% of theory).

What is claimed is:

1. A process for preparing a N-(3-amino-4-fluoro-phenyl)-sulphonamide, a N-(3-amino4-fluoro-phenyl)-carboxamide or a N-(3-amino-4-fluoro-phenyl)-carbamate of the general formula (I)

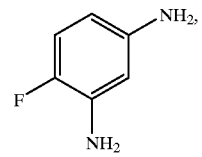

wherein

A represents $SO_2$, CO or $CO_2$ and

R represents in each case unsubstituted or substituted alkyl or aryl, comprising the step of reacting a 1-fluoro-2,4-diamino-benzene of the formula (II)

(II)

[structure II]

or an acid adduct thereof, with a sulphonyl chloride, a carbonyl chloride or a chloroformic ester of the general formula (III)

wherein

A and R are as defined above in the presence of an acid acceptor and in the presence of a diluent at a temperature between −20° C. and +100° C.

2. A process according to claim 1, wherein

A represents $SO_2$, CO or $CO_2$ and

R represents unsubstituted or cyano-, halogen- or $C_1$–$C_4$-alkoxy-substituted alkyl having 1 to 6 carbon atoms or represents unsubstituted or cyano-, nitro-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkoxycarbonyl- or di-($C_1$–$C_4$-alkyl)-amino-substituted aryl having 6 or 10 carbon atoms.

3. A process according to claim 1, wherein

A represents $SO_2$ or CO and

R represents in each case unsubstituted or cyano-, fluorine-, chlorine-, methoxy- or ethoxy-substituted methyl, ethyl, n- or i-propyl, n-, i-, s- or t-butyl, or represents unsubstituted or cyano-, nitro-, fluorine-, chlorine-, bromine-, methyl-, ethyl-, n- or i-propyl-, n-, i-, s- or t-butyl-, trifluoro-methyl-, methoxy-, ethoxy-, n- or i-propoxy-, difluoromethoxy-,trifluoromethoxy-, methylthio-, ethylthio-, n- or i-propylthio-, trifluoromethylthio-, methylsulphinyl-, ethylsulphinyl-, n- or i-propylsul phinyl-, trifluoromethylsul phinyl-, methylsul phonyl-, ethylsulphonyl-, n- or i-propylsulphonyl-, trifluoromethylsulphonyl-, methoxycarbonyl-, ethoxycarbonyl-, n- or i-propoxycarbonyl-, dimethylamino- or diethylamino-substituted phenyl.

4. A process according to claim 1, wherein the acid acceptor is pyridine.

5. A process according to claim 1, wherein from 0.9 to 1.5 moles of the sulphonyl chloride or the carbonyl chloride of the formula (III) and from 1.0 to 2.0 molar equivalents of the acid acceptor are employed per mole of 1-fluoro-2,4-diamino-benz ne of the formula (II).

6. A process according to claim 1, comprising the steps of (i) mixing the 1-fluoro-2,4-diamino-benzene of the formula (II) at room temperature with a diluent and an acid acceptor, and (ii) metering in with stirring of the mixture, the sulphonyl chloride, the carbonyl chloride or the chloroformic ester.

* * * * *